United States Patent [19]
Wachs et al.

[11] Patent Number: 4,559,365
[45] Date of Patent: Dec. 17, 1985

[54] IRON CARBIDE ON TITANIA SURFACE MODIFIED WITH GROUP VA OXIDES AS FISHER-TROPSCH CATALYSTS

[75] Inventors: Israel E. Wachs, Bridgewater; Rocco A. Fiato, Scotch Plains; Claudio C. Chersich, Englewood Cliffs, all of N.J.

[73] Assignee: Exxon Research and Engineering Co., Florham Park, N.J.

[21] Appl. No.: 626,068

[22] Filed: Jun. 29, 1984

[51] Int. Cl.$^4$ ................................................. C07C 1/04
[52] U.S. Cl. ..................................... 518/717; 518/720; 518/721
[58] Field of Search .......................... 518/717, 720, 721

[56] References Cited
U.S. PATENT DOCUMENTS
4,455,395  6/1984  Bussemeier et al. ................. 518/721

FOREIGN PATENT DOCUMENTS
300294  11/1928  United Kingdom ................. 518/721

OTHER PUBLICATIONS
Vannice, J of Catalysis 74, 199–202 (1982).
Niemantsverdriet et al., J. Phys. Chem. 84, 3363–3370.
Tatarchuk et al., J of Catalysis, 70, 308–322 (1981).

Primary Examiner—Howard T. Mars
Attorney, Agent, or Firm—Edward M. Corcoran

[57] ABSTRACT

Catalysts comprising iron carbide on a surface modified titania support wherein said support comprises a surface modifying oxide of tantalum, niobium, vanadium and mixtures thereof supported on said titania wherein at least a portion of said surface modifying oxide is in a non-crystalline form. These catalysts are useful for Fischer-Tropsch hydrocarbon synthesis reactions. Preferably, at least about 25 wt. % of said surface modifying oxide will be in a non-crystalline form.

11 Claims, No Drawings

IRON CARBIDE ON TITANIA SURFACE MODIFIED WITH GROUP VA OXIDES AS FISHER-TROPSCH CATALYSTS

BACKGROUND OF THE INVENTION

FIELD OF THE INVENTION

This invention relates to catalyst compositions of matter comprising iron carbide supported on a surface modified titania support. More particularly, this invention relates to Fischer-Tropsch catalyst compositions comprising iron carbide supported on a surface modified titania support, wherein said support comprises a surface modifying oxide of tantalum, vanadium, niobium or mixture thereof supported on the surface of said titania and wherein at least a portion of said surface modifying oxide is in a non-crystalline form.

BACKGROUND OF THE DISCLOSURE

The use of iron-titania mixtures as Fischer-Tropsch catalysts for converting mixtures of CO and $H_2$ to hydrocarbons is well-known to those skilled in the art. For example, U.S. Pat. No. 2,543,327 discloses titania promoted iron oxide for Fischer-Tropsch synthesis wherein the iron oxide is in the form of naturally occurring magnetite and preferably as Alan Wood ore. In this disclosure a typical catalyst is shown as prepared by mixing about 13,600 grams of Alan Wood ore with 98 grams of titania and 216 grams of potassium carbonate used as a promoter. The ratio of hydrogen to carbon monoxide disclosed as being preferably at least 2/1 and the results show that the catalyst has relatively poor activity with a large selectivity towards the production of methane and very little selectivity towards the production of $C_2+$ hydrocarbons. That is, the Fischer-Tropsch product was primarily methane. Similarly, British Pat. No. 1,512,743 also discloses a titania promoted, massive iron type of Fischer-Tropsch catalyst wherein iron oxide is mixed with titanium oxide, zinc oxide and potassium carbonate with the resulting mixture being sintered and then reduced for many hours at 500° C. Although this catalyst has relatively reasonably activity with regard to conversion of the CO and $H_2$ mixture, the product was primarily (i.e., about 73%) olefinic, unsaturated $C_2/C_4$ hydrocarbons and with only about 10% of $C_2/C_4$ saturated hydrocarbons or alkanes being produced. U.S. Pat. Nos. 4,192,777 and 4,154,751 while directed towards the use of potassium promoted Group VA metal cluster catalysts in Fischer-Tropsch synthesis reactions, suggest that iron supported on titania would be useful Fischer-Tropsch catalysts but do not disclose the preparation of same. In their examples, they disclose iron on various supports other than titania with the amount of iron on the support generally being less than about 5 percent. U.S. Pat. No. 4,261,865 discloses an iron titanate-alkali metal hydroxide catalyst for preparing alpha-olefins for mixtures of CO and $H_2$. That is, the catalyst is not iron supported on titania along with an alkali metal hydroxide but rather an iron titanate compound.

Another example of a titania-promoted massive iron catalyst for Fischer-Tropsch synthesis may be found in the Volume 17, No. 3-4 React. Kinet. Catal. Lett., pages 373-378, (1971) titled "Hydrocondensation of $CO_2$ (CO) Over Supported Iron Catalysts". This article discloses an iron oxide, titania, alumina, copper oxide catalyst promoted with potassium. Similarly, in European patent application EP 0 071770 A2 Fischer-Tropsch catalysts are disclosed which include iron-titania catalysts wherein the iron to titania ratio can be greater than 1/10. The actual iron-titania catalyst is not an iron supported on titania catalyst but an iron/titania catalyst produced by a coprecipitation technique wherein the active iron catalytic component is distributed throughout a titanium oxide matrix. Thus, the resulting catalyst was not iron supported on titania but rather a bulk phase iron/titania mixture which, when used for Fischer-Tropsch synthesis, produced predominantly olefins. The amount of olefins produced was generally greater than about 80% of the total hydrocarbon product.

With regard to iron/titania catalysts for Fischer-Tropsch wherein the iron is supported on titania, a 1982 article by Vannice, *Titania-Supported Metals as CO Hydrogenation Catalysts,* J. Catalysis, v. 74, p.199-202 (1982), discloses the use of an iron/titania catalyst for Fischer-Tropsch synthesis wherein the amount of iron, calculated as metallic iron, is 5 percent of the iron/titania composite and the catalyst shows extremely little activity for Fischer-Tropsch synthesis. An article by Reymond et al, *Influence of The Support or of an Additive on The Catalytic Activity in The Hydrocondensation of Carbon Monoxide by Iron Catalysts* in "Metal-Support and Metal-Additive Effects in Catalysis", B. Imelik et al (Eds), Elsevier, Netherlands, p.337-348 (1982), also discloses the use of iron/titania Fischer-Tropsch catalysts wherein the iron is supported on the titania.

U.S. Pat. No. 4,149,998 to Tauster et al. relates to heterogeneous catalysts consisting of Group VIII metals, including iron, dispersed on oxide carriers selected from the group consisting of Ti, V, Nb, Ta and mixtures thereof and zirconium titanate and $BaTiO_3$. However, there is no suggestion in this patent that the catalytic metal be dispersed on a surface modified titania.

SUMMARY OF THE INVENTION

It has now been discovered that catalysts comprising iron carbide supported on a surface modified titania support wherein said support comprises a surface modifying oxide of tantalum, niobium, vanadium and mixture thereof supported on the surface of said titania and wherein at least a portion of said surface modifying oxide is in a non-crystalline form are useful catalysts for Fischer-Tropsch hydrocarbon synthesis. Moreover, Fischer-Tropsch reactions conducted with these catalysts have been found to result in increased olefin and decreased methane make compared to Fischer-Tropsch catalysts comprising iron supported on titania wherein the surface of the titania has not been modified with a Group VA modifying oxide. Further, the catalysts of this invention produce a greater amount of heavier products and exhibit superior catalyst maintenance than similar catalysts on titania whose surface has not been modified with a Group VA oxide.

In a preferred embodiment at least about 25 wt. % of the surface modifying oxide of tantalum, niobium, vanadium or mixture thereof present on the titania surface will be in a non-crystalline form. In a particularly preferred embodiment, the catalyst will be pretreated with CO at elevated temperature prior to use.

DETAILED DESCRIPTION

The term surface modified titania as used herein refers to titania whose surface has been modified by an oxide of niobium, vanadium, tantalum and mixture thereof in an amount such that the modified support exhibits properties different from titania whose surface has not been modified and also different from bulk niobia, tantala, vanadia and mixture thereof. Concomitantly, the final catalyst composition will exhibit properties different from iron carbide supported on unmodified titania or on bulk niobia, tantala, vanadia and mixture thereof.

Thus, the catalyst support useful for preparing the catalysts of this invention comprise titania whose surface has been modified with an oxide of a Group VA metal (vanadium, niobium, tantalum and mixture thereof). That is, the surface of the titania has been modified by an oxide of vanadium, niobium, tantalum and mixture thereof in an amount such that the catalyst exhibits properties different from titania whose surface has not been modified and different from bulk oxides of vanadium, niobium, tantalum and mixture thereof. Those skilled in the art know that the oxides of niobium, tantalum, vanadium and mixtures thereof are crystalline in their bulk form. Thus, at least a portion of and preferably at least about 25 wt. % of the Group VA metal oxide will be in a non-crystalline form. This will be accomplished if the metal oxide loading on the titania broadly ranges between about 0.5 to 25 wt. % of the total catalyst weight.

In the catalyts of this invention the iron carbide is supported on the surface modified titania. Consequently, the catalysts of this invention are prepared by a two-step sequential process wherein the surface modified titania support is prepared first, followed by depositing the iron carbide or iron carbide precursor on the support. Thus, in the first step an oxide or precursor thereof of a metal selected from the group consisting of niobium, tantalum, vanadium and mixture thereof is deposited on the titania to form either the surface modified support or, in the case of one or more precursors, a support precursor. The support precursor will then be calcined to oxidize the oxide precursor and form a support comprising titania whose surface has been modified by an oxide of a metal selected from the group consisting of niobium, tantalum, vanadium and mixture thereof wherein at least a portion of said surface modifying oxide is in a non-crystalline form.

The catalyst support precursors of this invention may be prepared by techniques well-known in the art, such as incipient wetness, impregnation, etc., the choice being left to the practitioner. When using the impregnation technique, the impregnating solution is contacted with the titania for a time sufficient to deposit the oxide precursor material onto the titania either by selective adsorption or alternatively, the excess solvent may be evaporated during drying leaving behind the precursor salt. If an impregnation or incipient wetness technique is used to prepare a support precursor of this invention, the transition metal oxide salt solution used may be aqueous or organic, the only requirement being that an adequate amount of precursor compound for the selected Group VA transition metal oxide or oxides be soluble in the solvent used in preparing this solution.

The support precursor composite will then normally be dried at temperatures ranging from about 50°-300° C. to remove the excess solvent and, if necessary, decompose the salt if it is an organic salt to form a catalyst precursor. The support precursor composite is then converted into the surface modified titania support by calcining at temperatures of from about 150° to 800° C. and preferably 300°-700° C. in a suitable oxidizing atmosphere such as air, oxygen, etc. The time required to calcine the composite will, of course, depend on the temperature and in general will range from about 0.5-7 hours. Reducing atmospheres may also be used to decompose the transition metal oxide precursors, but the resulting composite will then require subsequent calcination to convert the reduced metal component to the oxide form.

The supports of this invention will generally have metal oxide loadings of from about 0.5 to 25 wt. % metal oxide on the titania based on the total support composition, preferably from about 1 to 15 wt. %, more preferably from about 2-10 wt. % based on the total support composition.

It is important to this invention that the iron carbide is supported on and not merely mixed with the surface modified titania support.

The catalyst will be prepared by depositing a suitable iron precursor component onto the surface modified titania support from a precursor solution using any of the well-known techniques such as incipient wetness, multiple impregnation, pore-filling etc., the choice being left to the convenience of the practitioner. As has heretofore been stated, it is important for the iron precursor to be deposited onto the support as opposed to other methods for catalyst preparation such as co-precipitation or physical mixtures. After impregnation, the impregnate is dried to remove excess solvent and/or water therefrom. The dry impregnate can then be converted to a catalyst of this invention employing a number of different methods. In one method, the impregnate will be converted directly to a catalyst of this invention by contacting same with a CO containing reducing gas, preferably a reducing gas containing a mixture of CO and $H_2$. Thus, it will be appreciated to those skilled in the art that the catalyst of this invention can be formed from the impregnate in-situ in a Fischer-Tropsch hydrocarbon synthesis reactor. However, it is preferred to employ a sequential treatment of first contacting the dry impregnate with an $H_2$ containing reducing gas that does not contain CO to reduce the impregnate, followed by contacting the reduced impregnate with CO or a CO containing gas such as a mixture of CO and $H_2$ to form the catalyst of this invention. As a practical matter, it may be commercially advantageous to form the catalyst of this invention by subjecting the impregnate to calcining to convert the supported iron precursor component to iron oxide, followed by subsequent reduction and formation of the catalyst of this invention.

Promoter metals such as potassium or other alkali metals may be added via impregnation, etc. before the composite is contacted with a reducing atmosphere and/or CO containing gas to form the catalyst of this invention. In general, the amount of promoter metal present will range from about 0.5 to 5 wt. % based on the amount of iron (calculated as $Fe_2O_3$) supported on the titania.

If one desires to obtain a catalyst of this invention via a supported iron oxide route, then the dry impregnate will be calcined in air or other suitable oxidizing atmosphere at a temperature of from about 120° to 300° C. for a time sufficient to convert the supported iron precursor component to iron oxide. After the iron/surface modified titania impregnate has been calcined to convert the supported iron precursor compound to iron oxide, the iron oxide/titania composite, with or without one or more promoter metals, is reduced in a hydrogen-

TABLE 1

| | 4 wt. % Iron on Titania | | 4 wt. % Iron on Titania Surface Modified With An Oxide of Vanadium | |
|---|---|---|---|---|
| Run | A | B | C | D |
| Temp. °C. | 305 | 315 | 290 | 305 |
| % CO Conversion | 47 | 60 | 49 | 70 |
| Wt. % Selectivity ($CO_2$ Free) | | | | |
| $CH_4$ | 21.0 | 24.4 | 16.1 | 17.8 |
| $C_2^=$ | 0.4 | 0.6 | 2.7 | 2.8 |
| $C_2^°$ | 16.1 | 16.2 | 20.2 | 16.8 |
| $C_3^=$ | 11.7 | 9.7 | 16.6 | 18.6 |
| $C_3^°$ | 13.7 | 12.7 | 14.4 | 16.5 |
| $C_4^=$ | 2.5 | 3.0 | 1.9 | 2.0 |
| $C_4^°$ | 7.1 | 7.4 | 8.1 | 10.9 |
| $C_5^+$ | 27.5 | 26.0 | 20.0 | 14.6 |

Conditions: 1:1 $H_2$:CO, 500 v/v/hr, 300 psig, pretreatment with $H_2$ at 500° C. for 5 hr. $C_5^+$ determined by nitrogen internal standard method.

The activity and carbon number distributions for the unmodified $Fe/TiO_2$ and the V and Nb surface modified $Fe/TiO_2$ catalysts during Fischer-Tropsch synthesis are presented in Table 2. The addition of V and Nb affected the activity and selectivity of the $Fe/TiO_2$ catalysts. The incorporation of V and Nb to the $TiO_2$ surface increased and decreased the conversion of CO, respectively. The stability of the modified catalysts was superior to that of the unmodified $Fe/TiO_2$ catalyst (less coking). The V and Nb modified $Fe/TiO_2$ catalysts substantially decreased the $CH_4$ yield and increased the $C_5^+$ yield. Whereas $Fe/TiO_2$ yields substantial amounts of paraffins (70-90%) paraffins in hydrocarbon) the V and Nb modified $Fe/TiO_2$ catalysts produced substantial amounts of olefins and low amounts of paraffins. In addition, XRD analysis of the spent V and Nb modified $Fe/TiO_2$ catalysts did not show the presence of $FeTiO_3$ in the catalysts. Thus, the addition of V and Nb to the surface of the $TiO_2$ altered the $Fe-TiO_2$ interaction and the nature of the products obtained from such a catalyst during Fischer-Tropsch synthesis.

TABLE 2

| | 4% $Fe/TiO_2$ | 4% Fe($TiO_2$ + V oxide) | 4% Fe($TiO_2$ + Nb oxide) |
|---|---|---|---|
| % CO Conversion | 27.0 | 34.3 | 20.1 |
| $C_1$ | 21.0 | 13.0 | 14.6 |
| $C_2$ | 17.0 | 21.5 | 15.0 |
| $C_3$ | 29.0 | 12.0 | 11.9 |
| $C_4$ | 9.0 | 8.0 | 6.0 |
| $C_5^+$ | 24.0 | 45.5 | 52.5 |

CONDITIONS: 270° C., 300 psia, 500-600 V/V/M, $H_2$:CO = 1

What is claimed is:

1. A process for producing hydrocarbons, including alkane hydrocarbons, from gaseous feed mixtures of CO and $H_2$ comprising contacting said feed, at a temperature ranging from about 200° to 350° C. and for a time sufficient to convert at least a portion of said feed to alkane hydrocarbons, with a catalyst comprising iron carbide supported on a surface modified titania support wherein said support comprises an oxide of a metal selected from the group consisting of niobium, vanadium, tantalum and mixture thereof supported on titania wherein at least a portion of said supported oxide is in a non-crystalline form.

2. The process of claim 1 wherein said catalyst contains one or more alkali promoters.

3. The process of claim 2 wherein the amount of iron carbide, calculated as iron, ranges from about 2 to 20 wt. % of the total catalyst composition.

4. The process of claim 3 wherein at least about 25 wt. % of said supported oxide is in non-crystalline form.

5. The process of claim 4 wherein the amount of supported iron carbide, calculated as iron, ranges from about 4 to 10 wt. % of the total catalyst composition.

6. A process for producing hydrocarbons, including alkane hydrocarbons, from gaseous feed mixtures of CO and $H_2$ comprising contacting said feed, a temperature ranging from about 200°-350° C. and for a time sufficient to convert at least a portion of said feed to alkane hydrocarbons, with a catalyst comprising iron carbide supported on a surface modified titania support wherein said support comprises an oxide of a metal selected from a group consisting of niobium, vanadium, tantalum and mixture thereof supported on titania wherein at least a portion of said supported oxide is in a non-crystalline form, said catalyst having been formed by a process comprising the steps of:
   (a) depositing an iron precursor compound on the surface modified titania support in an amount such that the final catalyst will contain supported iron in an amount of at least about 2 milligrams of iron, calculated as $Fe_2O_3$, per square meter of support surface;
   (b) calcining the iron precursor supported on the surface modified titania support produced in step (a) for a time sufficient to decompose said iron precursor material and convert at least a portion of said supported iron to $Fe_2O_3$ and form a calcined composite;
   (c) contacting said calcined composite formed in step (b) with hydrogen at elevated temperature for a time sufficient to convert at least a portion of said supported iron to a reduced composite; and
   (d) contacting said reduced composite formed in (c) with CO at elevated temperature of at least about 200° C. for a time sufficient to form said catalyst.

7. The process of claim 6 wherein said reduced composite is contacted with CO at a temperature broadly ranging from 200°-500° C. prior to use.

8. The process of either of claims 6 or 7, wherein said catalyst contains one or more alkali metal promoters.

9. The process of claim 8 wherein the amount of iron carbide present in said catalyst, calculated as iron, ranges from about 2 to 20 wt. % of the total catalyst composition.

10. The process of claim 9 wherein at least about 25 wt. % of said supported oxide of niobium, tantalum, vanadium or mixtures thereof is non-crystalline.

11. The process of claim 10 wherein the amount of supported iron carbide, calculated as iron, ranges from about 4 to 10 wt. % of the total catalyst composition.

* * * * *